(12) United States Patent
Nagata

(10) Patent No.: US 6,526,669 B2
(45) Date of Patent: Mar. 4, 2003

(54) APPARATUS FOR ACQUIRING HUMAN FINGER MANIPULATION DATA

(75) Inventor: Kazuyuki Nagata, Tsukuba (JP)

(73) Assignee: Agency of Industrial Science and Technology Ministry of International Trade and Industry, Tokyo (JP)

( * ) Notice: Subject to any disclaimer, the term of this patent is extended or adjusted under 35 U.S.C. 154(b) by 3 days.

(21) Appl. No.: 09/749,951

(22) Filed: Dec. 29, 2000

(65) Prior Publication Data
US 2001/0034947 A1 Nov. 1, 2001

(30) Foreign Application Priority Data
Apr. 26, 2000 (JP) ......................... 2000-126400

(51) Int. Cl.$^7$ ............. G01B 5/004; B25J 13/02; B25J 15/08
(52) U.S. Cl. ............. 33/503; 33/512; 700/245; 414/5
(58) Field of Search ......... 33/503, 512, 1 PT; 700/245, 318, 568.1, 568.11, 568.213; 414/5; 395/99; 340/407.1; 364/806; 345/157

(56) References Cited

U.S. PATENT DOCUMENTS

| | | | | |
|---|---|---|---|---|
| 4,571,839 A | * | 2/1986 | Fraser et al. | 33/1 PT |
| 4,682,805 A | * | 7/1987 | Reynolds | 294/86.4 |
| 4,897,924 A | * | 2/1990 | Tepley | 33/2 R |
| 4,905,001 A | * | 2/1990 | Pehner | 341/20 |
| 4,940,063 A | * | 7/1990 | Challis | 128/774 |
| 4,986,280 A | * | 1/1991 | Marcus et al. | 128/774 |
| 5,143,505 A | * | 9/1992 | Burdea et al. | 414/5 |
| 5,354,162 A | * | 10/1994 | Burdea et al. | 414/5 |
| 5,373,858 A | * | 12/1994 | Rose et al. | 128/782 |
| 5,471,996 A | * | 12/1995 | Boatright et al. | 128/782 |
| 5,482,056 A | * | 1/1996 | Kramer | 128/782 |
| 5,516,249 A | * | 5/1996 | Brimhall | 414/5 |
| 5,588,444 A | * | 12/1996 | Petragallo | 128/782 |
| 5,758,658 A | * | 6/1998 | Petragallo | 128/782 |
| 6,037,882 A | * | 3/2000 | Levy | 341/20 |
| 6,050,962 A | * | 4/2000 | Kramer et al. | 600/595 |
| 6,059,506 A | * | 5/2000 | Kramer | 414/5 |
| 6,088,017 A | * | 7/2000 | Tremblay et al. | 345/156 |
| 6,126,373 A | * | 10/2000 | Yee | 414/5 |
| 6,275,213 B1 | * | 8/2001 | Tremblay et al. | 345/156 |

FOREIGN PATENT DOCUMENTS

| | | | | |
|---|---|---|---|---|
| GB | 2275339 A | * | 8/1994 | G01B/7/03 |
| JP | 08006708 A | * | 1/1996 | G06F/3/00 |
| JP | 09054540 A | * | 2/1997 | G09B/9/00 |

OTHER PUBLICATIONS

Loncaric et al. Modular Dextrous Hand. UMCP. 1989.*
Griffin. Calibration and Mapping of a Human Hand for Dexterous Telemanipulation. Stanford University. 2000.*
LOncaric. Kinematics of Grasping with the Modular Dextrous Hand. 1989.*

(List continued on next page.)

Primary Examiner—Diego Gutierrez
Assistant Examiner—Gail Verbitsky
(74) Attorney, Agent, or Firm—Oblon, Spivak, McClelland, Maier & Neustadt, P.C.

(57) ABSTRACT

An apparatus for acquiring human finger manipulation data includes at least one finger motion detector consisting of a force sensor to be fitted on a human fingertip, at least three links and at least four angle detectors; and a base supporting the finger motion detector. The base can be attached to an external mount or a human hand. The force sensor is connected to the base through a link mechanism constituted by the links, and the angle detectors are attached at pivots between the links and optionally at a pivot between the link mechanism and the base. Three-dimensional motion of the finger is determined by measuring data of the angle detectors of the link mechanism, and fingertip contact force is measured by the force sensor. Up to five finger motion detectors, one for the thumb and each finger, can be supported on the base.

14 Claims, 3 Drawing Sheets

OTHER PUBLICATIONS

Ellis. Virtual Environments and Environmental Instruments. NASA Ames Research Center. 1996.*

EXOS Dextrous Hand Master. 1996.*

Kazuyuki Nagata, et al., "Development of a Fingertip–Type 6D Force Sensor and Error Evaluation of Contact Point Sensing," Journal of the Robotics Society of Japan, vol. 14, No. 8, Nov. 1996, pp. 137–144.

Shunji Shimizu, et al., "Development of Sensor Glove MKIII for Measuring Grasping Pressure Distribution," The 14$^{th}$ Science Lecture Meeting of the Robotics Society of Japan, 1996, pp. 1075–1076.

Super Glove Jr. marketed by Nissho Electronics Co., No date.

Cyber Glove marketed by Virtual Technologies, No date.

Dextrous Hand Master marketed by EXOS, No date.

Glove Scan System marketed by Nitta Co., No date.

Six–Axis Force Sensor IFS Series marketed by Nitta Co., No date.

NANO sensors marketed by BL Autotech, LTD., No date.

* cited by examiner

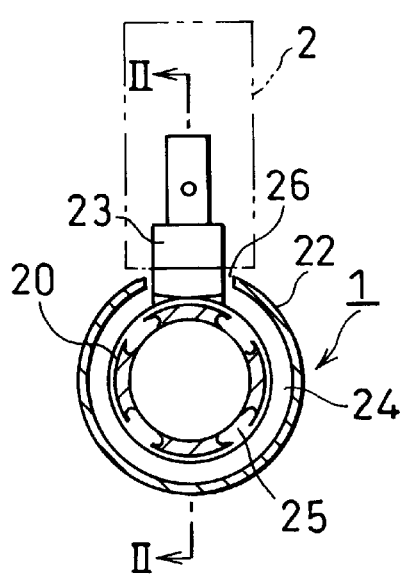
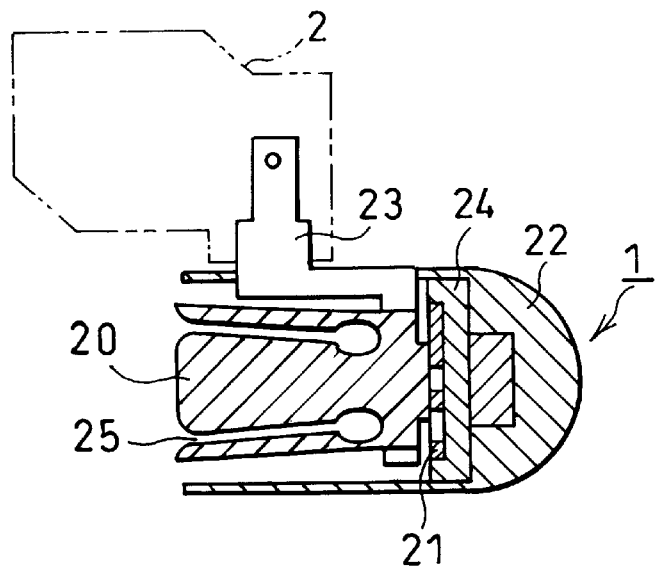
FIG.2(a)
FIG.2(b)
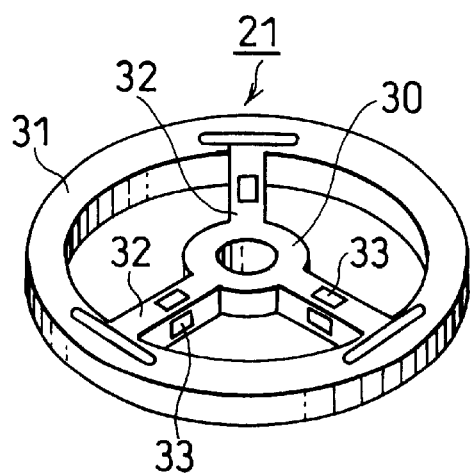
FIG.3

APPARATUS FOR ACQUIRING HUMAN FINGER MANIPULATION DATA

BACKGROUND OF THE INVENTION

1. Field of the Invention

This invention relates to an apparatus for acquiring human finger manipulation data useful for analyzing manipulative motions of the human hand in order to acquire data regarding motion of the human fingers and force acting on the fingertips for application of the data to control of a robot hand. (Except as otherwise obvious from the context, the term "finger" used in this specification includes the thumb).

2. Description of the Prior Art

Conventional devices developed for acquiring data regarding human finger motion include one type consisting of a glove having bending sensors whose resistance value changes with finger joint bending attached by sewing at the back of the finger joints (e.g., Super Glove Jr. marketed by Nissho Electronics Co. and Cyber Glove marketed by Virtual Technologies, Inc.) and another type that uses a parallel-link goniometer straddling the finger joints (e.g., Dextrous Hand Master marketed by EXOS).

For detecting distribution of pressures acting on the fingers and palm of the human hand, there has been developed a glove-like device worn on the fingers that has a distribution-type tactile sensor utilizing a pressure-sensitive conductive rubber or conductive ink sheet material sewn on the glove (e.g., Glove Scan System marketed by Nitta Co.).

Sensors developed for acquiring data regarding forces along six axes include types designed for mounting on the wrist of a robot (e.g., six-axis force sensor IFS series market by Nitta Co.) and types designed for mounting on a fingertip of a robot hand (e.g., NANO sensors marketed by BL Autotech, LTD.).

Analysis of the manipulative actions of the human hand based on acquired human hand grasp/manipulation data provides information that can be used to develop a robot hand grasping and manipulation algorithm that takes advantage of human knowledge and experience. Exploitation of human knowledge and experience opens the way to development of an algorithm for grasping and manipulating paper, cloth, cable and other flexible materials, which has so far been difficult to accomplish.

To achieve such grasping and manipulation it is essential to maintain dynamic balance and dynamic stability in the grasping operation. Since human finger motion data alone is therefore not sufficient, the contact forces acting on the fingertips must also be measured.

Humans manipulate objects chiefly with the fingertips. In acquiring human finger motion data, therefore, the importance of acquiring fingertip motion data far outweighs that of acquiring data regarding the motion of the individual joints.

Devices developed up to now for acquiring data regarding human finger motion include one that consists of an ordinary thin glove having bending sensors whose resistance value changes with finger joint bending attached by sewing at the back of the finger joints (e.g., Super Glove Jr. marketed by Nissho Electronics Co. and Cyber Glove marketed by Virtual Technologies, Inc.). When the wearer bends a finger, the device detects the finger joint angle from change in the resistance of the bending sensor.

A joint angle data detector has been developed which uses a parallel-link goniometer that straddles the finger joints with two sets of parallel links whose one side lies perpendicular to the finger links and whose jointed portions are equipped with angle detectors (Dextrous Hand Master marketed by EXOS).

These devices measure the individual joint angles of the human finger. In order to determine the motion of the fingertip, therefore, a complex calibration is required for calculating the effect length of the finger links.

As a device for detecting human finger tactile force, there has been developed a sensor glove having a distribution-type tactile sensor utilizing a pressure-sensitive conductive rubber or conductive ink sheet material sewn on the glove (Shimojo et al., "Development of Sensor Glove MKIII for measuring grasping pressure distribution," The 14$^{th}$ Science Lecture Meeting of the Robotics Society of Japan, 1996. Also, Glove Scan System marketed by Nitta Co.).

This sensor glove can detect distribution of pressures applied onto the fingers and palm. However, the detected force components are only those in the direction perpendicular to the surface of the sensor. When grasping/manipulating an object, a human being is known to utilize frictional force (tangential to the sensor surface) and moment at the fingertip surface. The sensor glove is therefore inadequate because it cannot detect frictional force tangential to the sensor surface or moment at the sensor surface.

When human hand grasping data are used directly for robot hand control, the data is preferably acquired using the same type of sensor as used by the robot hand. In this regard, it has been reported that as the sensor mounted on the fingertip of the robot hand it is important to use a six-axis force sensor (Nagata et al., "Development of a Fingertip-type 6D Force Sensor and Error Evaluation of Contact Point Sensing," Journal of the Robotics Society of Japan, Vol. 14, No. 8, 1996).

In view of this finding, the sensor used to detect contact force acting on the human finger should preferably be a six-axis force sensor that can be worn on the finger and is able to detect force and moment in three orthogonal directions.

Although six-axis force sensors for robots have been developed, even the smallest, the NANO sensors produced by BL Autotech, Ltd., measure 18 mm in diameter and 32.8 mm in length. Existing six-axis force sensors are therefore too large to be worn on the human fingertip.

In light of the foregoing circumstances, the inventor earlier developed a force sensor worn on the finger comprising a fingerstall for finger insertion, an elastic component and a finger cover for making contact with an object (U.S. patent application Ser. No. 09/610,968). This force sensor detects dynamic variation in contact force when the wearer manipulates an object. However, it is not able to measure three-dimensional motion of the fingers when an object is manipulated.

An object of the present invention is therefore to provide an apparatus for acquiring human finger manipulation data that, by accurately measuring not only fingertip contact force during grasping of an object with the fingertips but also three-dimensional motion of the fingers grasping the object, enables analysis of manipulative motions of the human hand.

SUMMARY OF THE INVENTION

To achieve this object, the present invention provides an apparatus for acquiring human finger manipulation data comprising at least one finger motion detector composed essentially of a force sensor capable of being fitted on a human fingertip, at least three links and at least four angle detectors; and a base supporting the finger motion detector, wherein the base is attachable to an external mount or a human hand, the force sensor is fittable on a human finger and connected to the base through a link mechanism constituted by the plurality of links, the at least four angle detectors are attached at pivots between the links constituting the link mechanism and optionally at a pivot between the link mechanism and the base, three-dimensional motion of the finger is determined by measuring data of the angle detectors of the link mechanism, and fingertip contact force is measured by the force sensor.

The angle detectors can be potentiometers, encoders or the like.

Not fewer than one and not more than five finger motion detectors can be supported on the base.

An inclination angle sensor can be installed on the base for measuring inclination of the base relative to vertical.

The base can be attached to a glove to be worn on a human hand.

The apparatus for acquiring human finger manipulation data according to the invention thus enables acquisition of data not only regarding contact forces acting on human fingertips but also regarding three-dimensional motion of the fingers at the time of grasping an object. By using the acquired data to analyze the manipulative actions of the human hand it becomes possible to develop a robot hand grasping and manipulation algorithm that takes advantage of human knowledge and experience, and by this to enable a robot hand to grasp and manipulate paper, cloth, cable and other flexible materials.

The above and other objects and features of the present invention will become apparent from the accompanying drawings and following detailed description.

BRIEF EXPLANATION OF THE DRAWINGS

FIG. 2(a) is a cross-sectional view showing an example of a six-axis force sensor, designed to fit on an operator's finger, used in the data acquisition apparatus of FIG. 1.

FIG. 2(b) is a cross-section taken along line II—II in FIG. 2(a).

FIG. 3 is a perspective view of an example of an elastic component used in the force sensor of FIG. 2.

DESCRIPTION OF THE PREFERRED EMBODIMENTS

Figure 1:
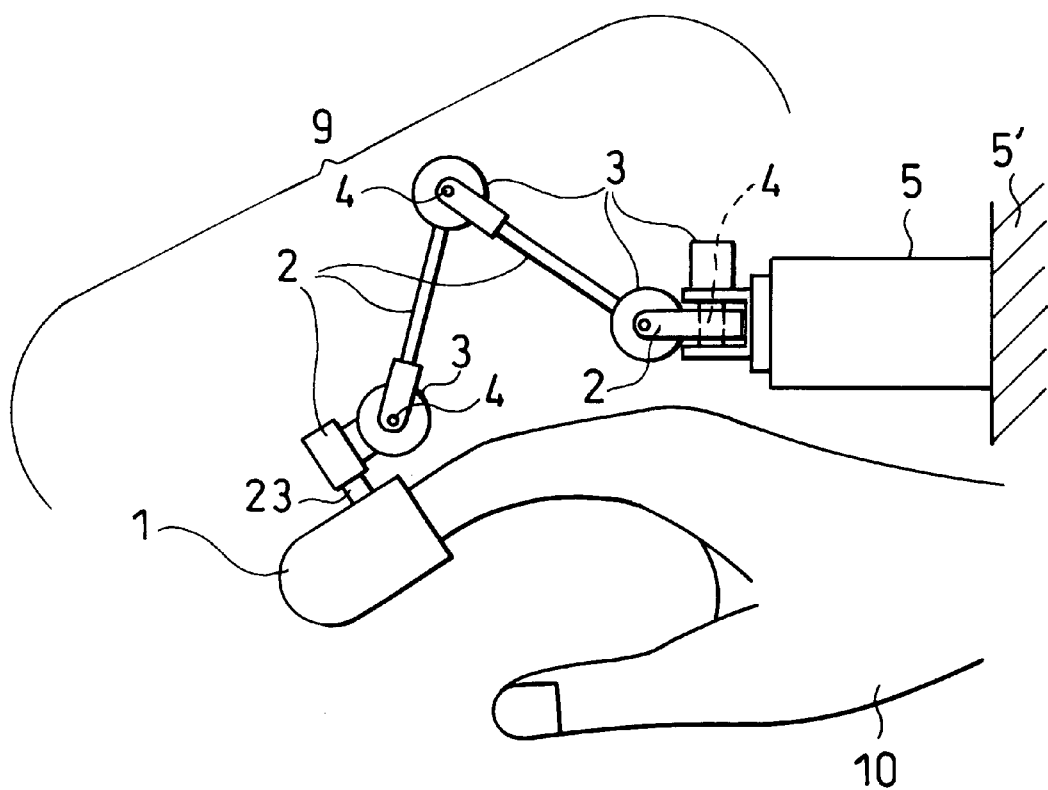
FIG. 1 is an explanatory view showing the basic configuration of an apparatus for acquiring human finger manipulation data according to a first embodiment of the present invention.

FIG. 1 is an explanatory view showing the basic configuration of a grasp data acquisition apparatus for the human hand according to the present invention. The apparatus comprises a finger motion detector 9 including a force sensor 1 to be worn on a human finger, at least three links 2 and at least four angle detectors 3, and a base 5.

Figure 4:
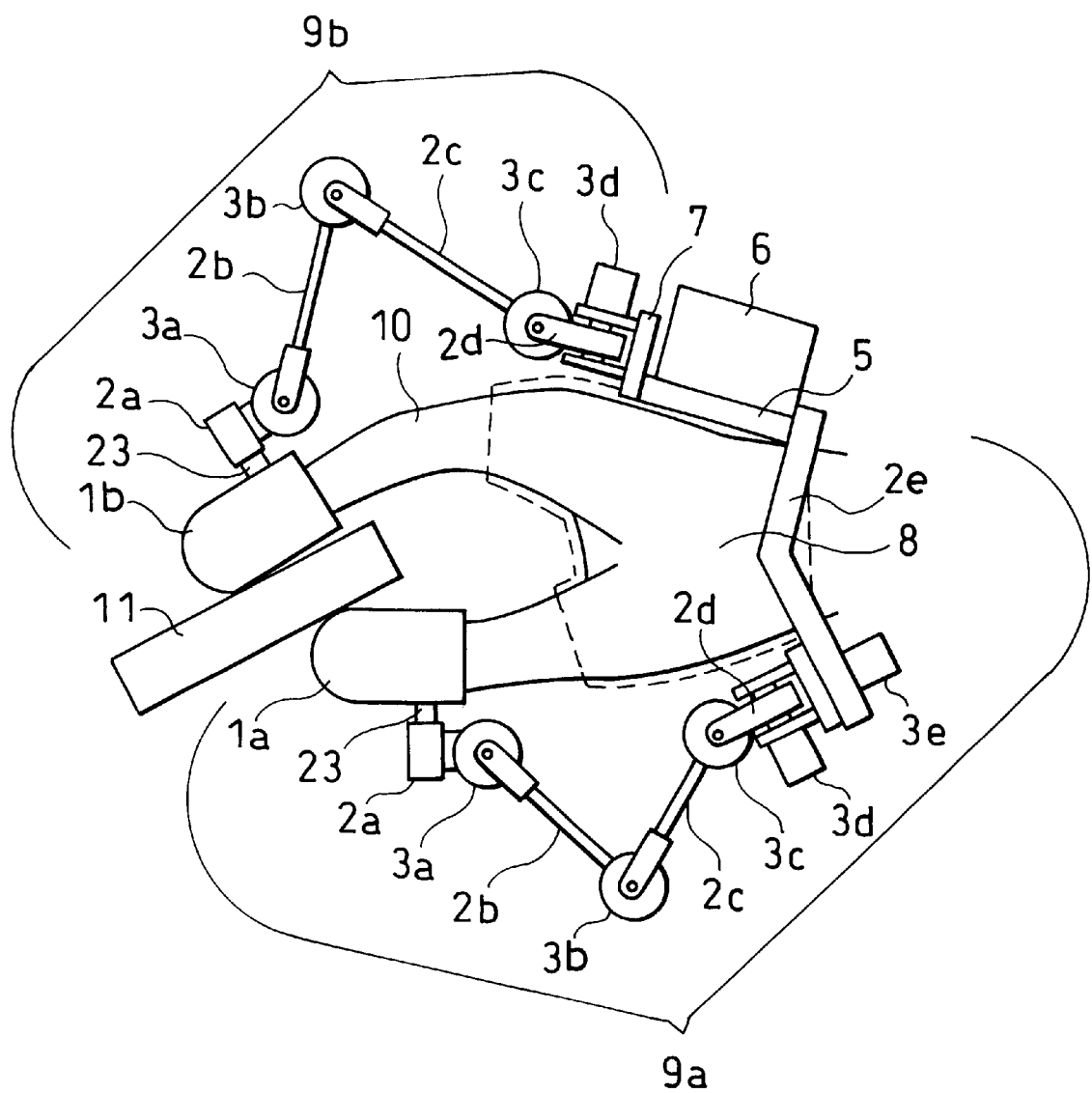
FIG. 4 is an explanatory view of an apparatus for acquiring human finger manipulation data that is a second embodiment of the present invention.

The finger motion detector 9 is supported by the base 5. In the embodiment illustrated in FIG. 1, the base 5 is fastened to an external mount 5'. Alternatively, it can be mounted on the hand of the operator as shown in the embodiment of FIG. 4 explained later. The links 2 are interconnected by pivots 4 to be rotatable relative to one another, thereby constituting a link mechanism. The distal link 2 of the link mechanism is connected to the force sensor 1 and the proximal link 2 thereof is connected through a pivot to the base 5.

The angle detectors 3 are used to measure finger motion. One is provided at the pivot 4 between each adjacent pair of links 2 and one at the pivot 4 between the proximal link of the link mechanism and the base 5. The angle detectors 3 can be conventional potentiometers, encoders or the like.

FIGS. 2(a) and 2(b) show an example of the force sensor 1 used in the apparatus for acquiring human finger manipulation data of the present invention. As shown, the force sensor 1 includes a fingerstall 20, an elastic component 21, a finger cover 22 and a link mounting lug 23.

As shown in FIG. 3 by way of example, the elastic component 21 is structured for ready distortion by specific force components. In the illustrated structure, the elastic component 21 is formed of a base 30 and a ring 31 interconnected by three sectionally square beams 32. Each beam 32 has strain gauges 33 attached one to each of its four lateral surfaces. When an external force is exerted on the elastic component 21, the beams 32 distort and the strain gauges 33 produce electric signals in proportion to the distortion. The force components can therefore be read out in the form of electric signals.

A strain stiffness matrix expressing the relationship between the six-axis forces (forces and moments in three orthogonal directions) acting on the elastic component 21 and the outputs of the strain gauges of each beam is generated in advance by calibration and used to convert the outputs of the strain gauges into force data. The six-axis forces exerted on the elastic component 21 can therefore be calculated from the output signals of the strain gauges using the strain stiffness matrix.

The fingerstall 20 is for receiving the tip of the operator's finger. It is made of an elastic material such as engineering plastic, phosphor bronze, spring steel or the like and is formed with slits 25 to facilitate insertion of different-sized fingertips. The fingerstall 20 is connected to the base 30 of the elastic component 21.

As shown in FIGS. 2(a) and 2(b), the fingerstall 20 is also connected to the distal link 2 of the link mechanism through the link mounting lug 23. The finger cover 22, the member that makes contact with the manipulated object, is connected to the ring 31 of the elastic component 21 through a mounting block 24. The finger cover 22 is formed with a cutout 26 so as to avoid contact with the link mounting lug 23.

FIG. 4 is an explanatory view of an apparatus for acquiring human finger manipulation data that is a second embodiment of the present invention. The finger motion detectors 9a and 9b shown in FIG. 4 are substantially identical to the finger motion detector 9 of FIGS. 1–3 in basic structure but the common base 5 is fastened to a glove 8 worn on a human hand rather than to the external stationary member 5'.

The glove 8 is indicated by a broken line in FIG. 4, as if transparent, so as to make it easier to understand the relationship between the apparatus for acquiring human finger manipulation data and the fingers. Although the illustrated embodiment has only the two finger motion detectors 9a and 9b associated with the thumb and index finger, this is solely for easier explanation of the operating principle, and finger motion detectors like that for the index finger designated by reference symbol 9b can be incorporated in association with the other fingers as required. The finger portions of the glove 8 are cut short and the base 5 is fastened to the part at the back of the hand by sewing. An inclination angle sensor 6 is attached to the base 5.

After the operator has put on the glove 8 and inserted a fingertip into each force sensor 1 (1a, 1b) of the apparatus according to this embodiment, monitoring of the contact force acting on the fingers and the motion of the fingers becomes possible. Explanation will be made first with regard to the finger motion detector 9a associated with the thumb. Three angle detectors 3 are installed at the carpometacarpal (CM) joint (at the root of the thumb) and one at each succeeding joint to enable measurement of motions in three directions of freedom (opposition, adduction/abduction, flexion/extension) at the CM joint, motions in one direction of freedom (flexion/extension) at the metacarpophalangeal (MP) joint (at middle of thumb), and motions in one direction of freedom (flexion/extension) at the interphalangeal (IP) joint (at end of thumb).

More specifically, three angle detectors are provided in mutually orthogonal orientation in the vicinity of the thumb CM joint, from the base 5 on through a link 2e: an angle detector 3e for detecting opposition motion of the CM joint, an angle detector 3d for detecting adduction/abduction of the CM joint, and an angle detector 3c for detecting flexion/extension of the CM joint.

The angle detector 3c at the thumb CM joint is connected through a link 2c to an angle detector 3b located above the thumb MP joint and this angle detector 3b is connected through a link 2b to an angle detector 3a in the vicinity of the thumb IP joint. A link 2a extending from the angle detector 3a in the vicinity of the thumb IP joint is connected to the link mounting lug 23 of a force sensor 1a. The angle detectors 3a, 3b and 3c measure thumb flexion/extension. Their axes of rotation are therefore oriented parallel to the axis of rotation of the thumb flexion/extension.

A finger motion detector 9b is associated with the index finger (and optionally each of the middle, ring and little fingers). Two angle detectors 3 are installed at the metacarpophalangeal (MP) joint (at the root of the finger) and one at each succeeding joint to enable measurement of motions in two directions of freedom (adduction/abduction, flexion/extension) at the MP joint, motions in one direction of freedom (flexion/extension) at the proximal interphalangeal (PIP) joint (at middle of finger), and motions in one direction of freedom (flexion/extension) at the distal interphalangeal (DIP) joint.

More specifically, an angle detector 3d for detecting adduction/abduction of the finger MP joint is attached to the base 5 through a block 7. The axis of rotation of the angle detector 3d lies perpendicular to the back of the hand, i.e., perpendicular to the upper surface of the base 5. An angle detector 3c for detecting flexion/extension of the finger MP joint is installed outward of the angle detector 3d. The angle detector 3c is connected through a link 2c to an angle detector 3b located above the finger PIP joint and the angle detector 3b is connected through a link 2b to an angle detector 3a in the vicinity of the finger DIP joint.

A link 2a extending from the angle detector 3a in the vicinity of the finger DIP joint is connected to the link mounting lug 23 of a force sensor 1b. The angle detectors 3a, 3b and 3c measure finger flexion/extension. Their axes of rotation are therefore oriented parallel to the axis of rotation of the finger flexion/extension.

The operation of the apparatus for acquiring human finger manipulation data will now be explained with reference to FIG. 4. The human operator puts on the glove 8 and inserts the thumb and fingers whose manipulative motions are to be measured into the fingerstalls 20 of the force sensors a and 1b. After donning the apparatus in this manner, the operator grasps/manipulates an object 11.

Specifically, the operator brings the finger covers 22 of the force sensors 1a and 1b into contact with the object 11 and applies force to the grasped object 11 through the fingerstalls 20, elastic components 21 and finger covers 22. The beams 32 of the elastic component 21 located between the fingerstall 20 and the finger cover 22 of each force sensor 1 are distorted in proportion to the amount of force applied to the grasped object 11.

The strain gauges 33 of the force sensors 1a and 1b convert the distortion into electric signals that are sent to a computer through an A/D converter (neither shown). Using a strain stiffness matrix generated beforehand by calibration, the computer calculates the forces exerted on the grasped object 11 from the outputs of the strain gauges 33.

The positions and the orientations of the fingertips are calculated using the data from the angle detectors 3a–3e and known dimensional parameters of the links 2a–2d. As a result, the motion of each fingertip can be calculated and plotted in an orthogonal coordinate system fixed to the base 5.

The data from the force sensors 1a and 1b is also plotted in the coordinate system after coordinate-transformation using the fingertip position and orientation data. The inclination angle sensor 6 is a conventional sensor for detecting inclination of the base 5 relative to the direction of gravitational force (vertical). The orientations of the fingertips relative to vertical are determined from the data obtained from the inclination angle sensor 6 and the angle detectors 3a–3e and used to compensate the force data from the force sensors 1a and 1b for the force of gravity.

While the present invention has been described in the foregoing with reference to specific embodiments of the apparatus for acquiring human finger manipulation data, it is not limited to the embodiments but can be modified within the scope of the appended claims.

As explained in the foregoing, according to the present invention, an apparatus for acquiring human finger manipulation data that is capable of measuring human finger motion and contact force acting on the fingertips comprises at least one finger motion detector constituted of a six-axis sensor that can be easily worn on the human fingertip, a link mechanism, and angle detectors.

The apparatus for acquiring human finger manipulation data enables acquisition of human hand grasp/manipulation data usable for analyzing the manipulative actions of the human hand and developing a robot hand grasping and manipulation algorithm that takes advantage of human knowledge and experience, which in turn opens the way to development of robot hands capable of grasping and manipulating paper, cloth, cable and other flexible materials that robots have heretofore found difficult to handle.

What is claimed is:
1. An apparatus for acquiring human finger manipulation data, the apparatus comprising:
   a finger motion detector composed essentially of at least three links, at least four angle detectors, and a six-axis force sensor adapted to being fitted on a fingertip of a human finger of a human hand of an operator, the six-axis force sensor comprising a fingerstall adapted to have the fingertip of the human finger of the human hand inserted therein, a finger cover having a mounting block and for making contact with an object, and an elastic structure disposed between the fingerstall and the finger cover, the finger cover being connected and fixed to the elastic structure via the mounting block; and a base supporting the finger motion detector, wherein the base is adapted to being attached to either an external mount or the human hand, wherein the six-axis force sensor is adapted to being fit on the human finger of the human hand of the operator and connected to the base through a link mechanism constituted by the at least three links, wherein the at least four angle detectors are attached at pivots between the at least three links constituting the link mechanism and optionally at a pivot between the link mechanism and the base, wherein a position and a posture of the fingertip of the human finger of the human hand of the operator is determined by measuring a motion of the link mechanism, and wherein fingertip contact force is measured by the six-axis force sensor.

2. The apparatus according to claim 1, wherein the angle detectors are potentiometers or encoders.

3. The apparatus according to claim 1, wherein not fewer than one and not more than five of the finger motion detectors are supported on the base.

4. The apparatus according to claim 2, wherein not fewer than one and not more than five of the finger motion detectors are supported on the base.

5. The apparatus according to claim 1, wherein the base is provided with an inclination angle sensor for measuring angles of inclination of the base relative to a reference coordinate system, the reference coordinate system consisting of a roll angle, a pitch angle, and a yaw angle.

6. The apparatus according to claim 2, wherein the base is provided with an inclination angle sensor for measuring angles of inclination of the base relative to a reference coordinate system, the reference coordinate system consisting of a roll angle, a pitch angle, and a yaw angle.

7. The apparatus according to claim 3, wherein the base is provided with an inclination angle sensor for measuring angles of inclination of the base relative to a reference coordinate system, the reference coordinate system consisting of a roll angle, a pitch angle, and a yaw angle.

8. The apparatus according to claim 1, wherein the base is attached to a glove adapted to be worn on the human hand of the operator.

9. The apparatus according to claim 2, wherein the base is attached to a glove adapted to be worn on the human hand of the operator.

10. The apparatus according to claim 3, wherein the base is attached to a glove adapted to be worn on the human hand of the operator.

11. The apparatus according to claim 4, wherein the base is attached to a glove adapted to be worn on the human hand of the operator.

12. The apparatus according to claim 5, wherein the base is attached to a glove adapted to be worn on the human hand of the operator.

13. The apparatus according to claim 6, wherein the base is attached to a glove adapted to be worn on the human hand of the operator.

14. The apparatus according to claim 7, wherein the base is attached to a glove adapted to be worn on the human hand of the operator.

* * * * *